United States Patent [19]

Person

[11] Patent Number: 4,642,333

[45] Date of Patent: Feb. 10, 1987

[54] IMMUNOLOGICALLY REACTIVE NON-GLYCOSYLATED AMINO ACID CHAINS OF GLYCOPROTEIN B OF HERPES VIRUS TYPES 1 AND 2

[76] Inventor: Stanley Person, 600 Locust La., State College, Pa. 16801

[21] Appl. No.: 622,496

[22] Filed: Jun. 20, 1984

Related U.S. Application Data

[63] Continuation-in-part of Ser. No. 532,996, Sep. 16, 1983, abandoned, which is a continuation-in-part of Ser. No. 506,986, Jun. 23, 1983, abandoned.

[51] Int. Cl.$^4$ ............................................. C07K 13/00
[52] U.S. Cl. ................................................... 530/350
[58] Field of Search .................. 260/112.5 R; 435/172; 536/27; 530/350

[56] References Cited

FOREIGN PATENT DOCUMENTS

0100521 7/1983 European Pat. Off. .

OTHER PUBLICATIONS

Chem. Abstr., vol. 97, (1982), 212464g.
Chem. Abstr., vol. 73, (1970), 95695z.
Chem. Abstr., vol. 84, (1976), 15505b.
Chem. Abstr., vol. 84, (1976), 146461g.
Chem. Abstr., vol. 99, (1983), 2836v.
Chem. Abstr., vol. 99, (1983), 154988j.
Chem. Abstr., vol. 97, (1982), 53465g.
Chem. Abstr., vol. 98, 210720j.
Chem. Abstr., vol. 98, (1983), 157635g.
Chem. Abstr., vol. 98, (1983), 32385u.
Molecular Cloning-A Laboratory Manual, T. Maniatis et al, (1981), pp. 135-139.
Cloned Viral Protein Vaccine for Foot-and-Mouth Disease, Science, vol. 214, Dec. 1981, pp. 1125-1129.
Nucleotide Sequences of Herpes Simplex Virus Type 1 (HSV-1), Affecting Virus Entry, Cell Fusion, and Production of Glycoprotein gB (VP7), DeLuca et al, Virology 122, pp. 411-423.
Person, S. et al., "Expression in Bacteria of gB-Glycoprotein-Coding Sequences of Herpes Simplex Virus Type 2", Gene 35, (1985): 279-287.
Bond, Vincent C. et al., "The Isolation and Characterization of Mutants of Herpes Simplex Virus Type 1 That Induce Cell Fusion", J. Gen. Virol., 61, (1982): 245-254.
Spivack, Jordan G. et al., "A Study of the Antiviral Mechanism of Action of 2-Deoxy-D-glucose: Normally Glycosylated Proteins Are Not Strictly Required for Herpes Simplex Virus Attachment But Increase Viral Penetration and Infectivity", Virology 123, (1982): 123-138.
Spear, Patricia G. et al., "Proteins Specified by Herpes Simplex Virus, IV, Site of Glycosylation and Accumulation of Viral Membrane Proteins", Proceedings of the National Academy of Sciences 66:3, (1970): 730-737.
Honess, Robert W. et al., "Proteins Specified by Herpes Simplex Virus, XIII, Glycosylation of Viral Polypeptides", Journal of Virology 16:5, (1975): 1308-1326.
Spear, Patricia G., "Membrane Proteins Specified by Herpes Simplex Viruses: I. Identification of Four Glycoprotein Precursors and Their Products in Type 1-Infected Cells", Journal of Virology 17:3, (1976): 991-1008.
Serafini-Cessi, Franca et al., "N-Acetylgalactosaminyltransferase Activity Involved in O-Glycosylation of Herpes Simplex Virus Type 1 Glycoproteins", Journal of Virology 43:1, (1983): 325-329.
Holland, Thomas C. et al., "Physical Mapping of the Mutation in an Antigenic Variant of Herpes Simplex Virus Type 1 by Use of an Immunoreactive Plaque Assay", Journal of Virology 46:2, (1983): 649-652.
Wenske, Elizabeth A. et al., "Glycosylation of Herpes Simplex Virus Type 1 gC in the Presence of Tunicamycin", Journal of Virology 46:1, (1983): 297-301.

*Primary Examiner*—Delbert R. Phillips
*Attorney, Agent, or Firm*—Wegner & Bretschneider

[57] ABSTRACT

Plasmids are constructed containing the nucleotide sequence for selectively expressing immunologically active amino acid chains of glycoprotein B of HSV-1 and HSV-2 and chains are prepared to serve in vaccines.

2 Claims, No Drawings

IMMUNOLOGICALLY REACTIVE NON-GLYCOSYLATED AMINO ACID CHAINS OF GLYCOPROTEIN B OF HERPES VIRUS TYPES 1 AND 2

This is a continuation-in-part of application Ser. No. 532,996, filed Sept. 16, 1983, now abandoned which is a continuation-in-part of application Ser. No. 506,986 filed June 23, 1983 now abandoned.

The present invention relates to vaccines for prophylaxis and treatment of Herpes simplex virus types 1 and 2, generally abbreviated as HSV-1 and HSV-2. More specifically it relates to application of recombinant DNA technology to production of plasmids containing the nucleotide sequence for expressing amino acid chains comprising sequences identical to those occurring in glycoprotein B of HSV-1 and HSV-2 to the exclusion of other gene sequences, to amino acid chains expressed thereby and their derivatives which produce an effective immunogenic response to HSV-1 or HSV-2 and vaccines based on the amino acid chain products produced thereby.

The invention provides DNA molecules which can be used to induce the synthesis of the protein part of glycoprotein B in a living prokaryotic and eukaryotic cell capable of having recombinant DNA introduced therein and recovered therefrom and capable of expressing such DNA molecule. The use of the recombinant DNA technology of this invention is cost efficient and the amino acid chain produced provides a synthetic prophylactic therapeutic agent without the hazard of contamination with live virus.

The DNA of Herpes simplex virus of type 1 and 2 contains 150 kb and has sufficient information to code for 100-200 proteins. About 30 of the proteins are present in the viral particle; the remaining encoded proteins are associated with replication and assembly of the virus inside the host cell. In addition to the DNA core surrounded by a protein coat, the virus possesses an outer membrane structure. That membrane is composed of lipids and viral-encoded glycoproteins. These glycoproteins are proteins with one or more saccharide chains initiated at particular amino acid residues. There are four HSV glycoproteins—gA/gB, gC, gD and gE, gA being a precursor to gB.

HSV probably enters a host cell by the fusion of the viral and cellular membranes and this fusion is mediated by gB. The virus replicates in the nucleus. During replication glycoproteins are synthesized and transported to the cell surface, with much of the glycoprotein projecting through the outside surface of the plasma membrane of infected cells. Since viral glycoproteins project outward from the viral and cellular surfaces they are first viral molecules encountered by HSV-specific antibodies.

Vaccines in general consist of the entire virus particle (live, attenuated or dead viruses) or structural proteins of the virus (subunit vaccines). Although there are reports of beneficial effects of live HSV vaccines, most experts do not advise this route because of the possibility that HSV has carcinogenic or cocarcinogenic activity and because the virus is generally not of the life-threatening type. Therefore subunit vaccines composed of one or more glycoproteins or their non-glycosylated amino acid chain or immunogenically active portion thereof present a more desirable alternative. The live vaccine is attractive because it would be inexpensive to produce; one needs very little since it multiplies after vaccination, but it is potentially dangerous. A subunit vaccine requires production of larger volumes (masses) of a protein and is more costly, but it is safer.

Viral glycoproteins and protein ingredients thereof synthesized in $E.\ coli$ by recombinant DNA techniques according to this invention are completely free of viral DNA. Only a single viral glycoprotein gene is present, not the entire viral DNA. Recombinant DNA technology removes risks due to live virus contamination from vaccine production.

Of the major viral glycoproteins only one, gB, has known biological functions and has been established to be essential for viral growth. In the Tables following the Examples, there are presented the DNA coding sequences of gB of HSV-1 and HSV-2. The present invention provides a nucleotide sequence capable of expressing the amino acid chain of the glycoprotein B. Insertion of the gene into a microorganism permits synthesis of the protein corresponding to HSV glycoprotein gB. Only the protein and not the saccharide part of gB is synthesized in bacteria, but the protein is the chief source of immunogenic determinants. For expression, a microorganism, typically a bacterium such as $E.\ coli$, is grown in a conventional growth medium containing the plasmid capable of expressing the desired amino acid chain. The purified HSV protein of this invention, extracted from the membrane fraction of the bacteria, can be injected into animals, e.g. rabbits, to produce antibodies against the protein. These antibodies produced in the animals in response to gB protein made in bacteria can be tested for their ability to inactivate (neutralize) viruses.

After maximization of HSV-gB expression in bacteria and demonstration of appropriate virus neutralization by antibodies produced against gB, the gB protein vaccine is tested in animals and can be finally evaluated in clinical trials. One injection of about 3 ug protein/kg in rabbits produces an antibody response.

Although the entire coding sequences of gB could be expressed in bacteria, there are practical reasons why expression of only a portion of immunologically active gB is desirable. There are two extensive hydrophobic regions, the signal and membrane-spanning regions (see Sequence Summary below) that if present could alter the three-dimensional conformation of gB expressed in the cytoplasm of $E.\ coli$. When the mature protein is present in the membranes of infected cells the signal sequence is enzymatically removed and the membrane-spanning residues are within the membrane. Remaining C-terminal residues on the cytoplasmic side of the membrane are inaccessible to antibodies. Therefore, no more than 750 N-terminal amino acid residues of a total of 903 are likely to be antigenically active as regards a vaccine.

Hydrophilic residues are likely to reside on the surface of a protein; these residues in regions of β-turns are candidates for antigenic determinants. However, since primary and tertiary structures are not linearly related, hydrophilic residues that form an antigenic site are not necessarily contiguous. Nonetheless, appropriately chosen contiguous residues 10 to 20 amino acids in length are often antigenic and can lead to the production of antibodies that combine with the native protein. Therefore the simplest vaccine is a short peptide with high antigenic activity whose sequence is derived from a knowledge of the nucleotide sequence of the gB gene.

HSV-1 PLASMIDS

A typical recombinant DNA clone of Herpes simplex virus type 1 of this invention, exemplified by the clone designated pKBXX, can be constructed by the following procedure. Purified DNA from the KOS strain is cleaved with the restriction endonuclease BamHI using reaction conditions as specified by the supplier of such enzymes. At the same time, vector DNA pBR322 (cf. Bolivar et al., Gene 2, 95–113, 1977) is cleaved with BamHI. The enzymes can be removed and inactivated by extraction with an organic solvent, the DNA precipitated in the cold with ethanol and vacuum dried to remove residual solvent. The BamHI-cut HSV-1 DNA is ligated to the similar cohesive ends in BamHI-cut pBR322 vector, having a unique BamHI site in a tetracycline-resistance gene (Tc$^r$). Ligation is conveniently accomplished by use of T4 DNA ligase at about 4° according to the conditions supplied by the manufacturer. Both the cutting and sealing reaction are carried out in a closed plastic vessel.

A similar sequence of reactions can be carried out, using again the KOS strain, by cleaving with a similar number of enzyme units of restriction endonuclease EcoRI and by subjecting the vector DNA pBR325 (Bolivar, Gene 4, 121–136; 1978) to cleavable with EcoRI. The enzymes are again removed and the EcoRI-cut HSV-1 is ligated to the similar ends in pBR325 which has a unique EcoRI site in a chloramphenicol-resistant (Cm$^r$) gene using comparable ligation conditions.

The plasmid pBR325 contains genes that specify drug resistance to ampicillin (Ap$^r$), tetracycline and chloramphenicol, and pBR322 specifies ampicillin and tetracycline-resistant genes. Following the introduction of the ligated mixtures into E. coli, vectors that are inferred to contain HSV-1 fragments are identified by resistance to ampicillin but sensitivity to (inability to grow in the presence of) chloramphenicol for pBR325 or tetracycline for pBR322. Drug resistance and other genes are almost always inactivated by the insertion of a foreign piece or unrelated DNA.

Recombinant plasmids containing the EcoRI-F or the BamHI-G fragment are identified by comparing the electrophoretic mobilities of HSV-1 inserts with published restriction maps of HSV-1 for these enzymes. Restriction fragments are denoted by capital letters of the alphabet (A to Z) in order of increasing mobilities on agarose gels, corresponding to decreasing nucleotide lengths. The same strain of HSV-1, i.e. KOS, will have only one restriction map for any one restriction endonuclease. However, a different strain of HSV-1, since it may have evolved quite separately from KOS, will share most, but not necessarily all, of the same restriction sites.

To identify subclones, especially of the EcoIRI-F fragment obtained from the KOS strain and the tsB5 strain, use is made of the coordinates for the EcoRI-F fragment of KOS.

A restriction map of the subclones of the EcoIRI-F fragment of HSV-1, strain KOS, shows the following restriction sites, using as restriction enzymes BamHI (B),
BstEII (T),
EcoRI (E),
HpaI (H),
KpnI (K),
PstI (P),
SalI (S), and
XhoI (X).

0.315 E; 0.317 P; 0.318 K; 0.320 B; 0.322 P; 0.323 K; 0.327 P; 0.328 H; 0.330 P; 0.330 S; 0.334 B; 0.335 S; 0.337 X; 0.338 H; 0.339 T; 0.340 B; 0.341 X; 0.343 S; 0.343 X; 0.344 P; 0.345 B; 0.346 K; 0.049 T; 0.350 P; 0.355 T; 0.356 P; 0.360 S; 0.368 P; 0.368 X; 0.372 X; 0.380 K; 0.382 T; 0.387 S; 0.388 P; 0.397 P; 0.398 X; 0.399 B; 0.403 X; 0.405 T; 0.409 K; 0.413 T; 0.414 B; 0.418 T; 0.419 S; 0.420 K; 0.422 E.

A comparison of the maps for the restriction endonuclease cleavage sites for the KOS strain and the temperature sensitive tsB5 strain shows sites specific for KOS at 0.318 K; 0.344 P; 0.355 T; and 0.413 T and specific for tsB5 at 0.331 H, 0.355 P, and 0.389 X.

A comparison between the restriction maps for EcoRI-F fragments and the tsB5 strain shows that the two strains share all of the sites except for 7 in that EcoRI-F fragment, which is enclosed by genome coordinates 0.315 to 0.422.

The genome of HSV-1 is a linear double-stranded DNA molecule of 150 kb. Therefore, 0.01 map units correspond to approximately 1.5 kb.

A plasmid designated pKEXX of HSV-1 gB was constructed which contains HSV-1 sequences from the BamHI site at 0.345 to the XhoI site at 0.372. A BamHI-G fragment with coordinates from the 0.345 site to the 0.399 site, is first prepared by the foregoing ligation procedure and then subjected to partial digestion with SalI and religated to delete SalI fragments. This yields fragment pKBG-BS3, with coordinates from the 0.345 BamHI site to the SalI site at 0.387. It contains two XhoI (0.368 and 0.372) sites. To obtain the desired sequences in pKBXX, pKBG-BS3 is subjected to a complete digest with BamHI and a partial digest with XhoI. Following agarose electrophoresis a 4.0 kb band corresponding to the 0.345 to 0.372 BamHI-XhoI fragment is seen and is electroeluted from the gel and ligated to BamHI, SalI cut pUC9. pUC9 is a 2.7 kb plasmid with an ampicillin-resistance gene and a multi-cloning site, cf (Vieira & Messing, Gene 19:259–268, 1982; Messing & Vieira, ibid: 269). The plasmid is commercially available from Bethesda Research Labs. The origin of replication of the plasmid and the ampicillin resistance gene are derived from pBR322 (approximately nucleotides 2067 to 4362). The remaining sequences of pUC9 (about 400 nucleotides) are derived from the beginning of the lac genes of E. coli. Specifically, the sequences contain a promoter (for RNA synthesis), a ribsosome-binding site (for protein synthesis), and an N-terminal fragment of the first gene product, $\beta$-galactosidase. The direction of RNA and protein synthesis is from left to right. The multiple cloning site contains the restriction sites HindIII-PstI-SalI-BamHI-SmaI-EcoRI (from left to right) that are inserted between sequences specifying amino acids 4 and 5 of E. coli $\beta$-galactosidase (see Table 3). It has been shown that $\beta$-galactosidase protein synthesis is independent of the sequences of amino acids near its N-terminal end (as long as the correct reading frame is maintained). Therefore, functional $\beta$-galactosidase is synthesized in a cell containing pUC9 plasmid DNA. The vector, having unique restriction sites immediately adjacent to the HSV-1 cloned sequences but not present in HSV-1 sequences, also allows the HSV-1 clone to be recloned into any other vector that contains the same restriction sites. For the purpose of constructing pKBXX, pUC9 DNA was treated with BamHI and SalI and HSV-1 sequences (BamHI to XhoI, 0.345 to 0.372)

are ligated to these sites. The appropriate clone (following transformation analysis) is identified by restriction mapping. It has been shown that the HSV-1 sequences contained within pKBXX are those in the listing of restriction sites for the restriction map given hereinabove.

It should be noted that SalI (G TCGA C) and XhoI (C TCGA G) cleave DNA at different sequences because their recognition sites differ at the terminal nucleotide sites, but they generate the same four-base, internal "sticky-end" site (TCGA). Therefore, an XhoI site can be cloned into a SalI site and this was done in pKBXX. AT the HSV-1 XhoI-pBR322 SalI junction the base sequences become CTCGAC, a hybrid site. This site is not cleaved by either of the enzymes used in the generation of the recombinant plasmid.

Nucleotides are numbered from 1 to 3997 in pKBXX in the right-to-left direction (XhoI to BamHI). All of the nucleotides in pKBXX have been sequenced using the M13 cloning vector, dideoxy chain-termination method. A summary of the sequence by nucleotide number follows.

| SEQUENCE SUMMARY | |
|---|---|
| 1 to ~375 | 5' extra sequences beginning with the XhoI site at 0.372 |
| ~375 to 499 | 5' mRNA regulatory sequences including two CAAT boxes beginning at nucleotides 406 and 443, and a TATA box at 476 |
| 499 to 789 | mRNA start sequences (starts at an A in the sequence CACCACAC - the first A is #501) to the first coding nucleotide (which begins with nucleotide #790) |
| 790 to 3498 | 903 amino acid coding sequences including an N-terminal hydrophobic leader and a membrane-spanning sequence, a C-terminal ionic sequence, and 9 sites for saccharide 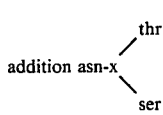 The region of the glycoprotein that would be outside of the cell surface is about 750 amino acids. |
| 3499 to 3549 | 3' noncoding sequences including polyA addition signal beginning at 3518 and probable polyA addition site at 3549 |
| 3549 to 3997 | 3' nonessential sequences to the BamHI site at 3992 (coordinate 0.345). |

The complete table of the nucleotide sequence of pKBXX appears in Table 1 and of the translation product in Table 2. The significant features of the peptide include an N-terminal, largely hydrophobic membrane-insertion or signal sequences, nine possible N-linked saccharide-addition sites, hydrophobic membrane-spanning sequences, and highly charged cytoplasmic anchor sequences (109 amino acids). N-terminal signal sequences are removed by a specific signal peptidase during glycoprotein synthesis to produce the mature peptide.

HSV-2 PLASMIDS

HSV-2 specifies a gene homologous to the gB gene of HSV-1. A typical recombinant DNA clone of Herpes simplex virus type 2 of this invention, exemplified by the clone designated p52BXX, can be constructed by the following procedures. Purified DNA from the HG52 strain is cleaved with the restriction endonuclease EcoRI using reaction conditions as specified by the supplier of this enzyme. At the same time, vector DNA pBR325 is cleaved with EcoRI. The enzymes are removed and inactivated by extraction with an organic solvent, the DNA precipitated in the cold with ethanol, and vacuum dried to remove residual solvent. The EcoRI-cut HSV-2 is ligated to the same cohesive ends in EcoRI-cut pBR325 vector, having a unique EcoRI site in a chloramphenicol-resistance gene. Ligation is conveniently accomplished by the use of T4 DNA ligase at about 4° C. according to the conditions supplied by the manufacturer.

The plasmid pBR325 contains genes that specify drug resistance to ampicillin, chloramphenicol and tetracycline. Following the introduction of the ligated mixtures into E. coli, cells containing vectors that are inferred to contain HSV-2 fragments are identified by their resistance to ampicillin (or tetracycline) and their sensitivity to (inability to grow in the presence of) chloramphenicol. Drug resistance and other genes are almost always inactivated by the insertion of a large piece of foreign DNA. A group of chloramphenicol-sensitive clones (colonies) was screened to determine those containing HSV-2 gB sequences. To do this, separate bacterial colonies are re-grown on a special filter paper overlaid onto a dish containing solidified growth medium. The resulting colonies are fixed in place and made permeable to externally added DNA by a NaOH treatment. This treatment also separates double-stranded DNA into single strands. A solution of radioactive single-stranded DNA derived from the coding sequences of HSV-1 gB is poured over the filter, the filter is incubated and extensively washed with an appropriate buffer. Nucleotide sequences of HSV-1 will only bind, and be retained on the filter, if the HSV-2 containing plasmid DNA in a particular colony contains hoimologous (essentially identical) nucleotide sequences. This process is called hybridization, meaning that the double-stranded DNA retained on the filter contains on radioactive strand of HSV-1 and a non-radioactive strand of HSV-2. The filter paper is exposed to X-ray film, and hybridization is detected as a dark spot in the position of the appropriate colony. In this way colonies were identified that contain a vector with HSV-2 EcoRI fragment designated p52EG. Two colonies gave intense hybridization and contained an insert whose mobility was indistinguishable from that of EcoRI-G fragment (measured by comparision with HSV-1 EcoRI-F fragment which appeared to share the same coordinates). The insert also contained a unique HindIII site characteristic of EcoRI-G fragment. The original clone (p52EG) was cleaved with BamHI and HindIII and cloned into the same sites of pUC9, following gel elution of the fragment, and was designated p52EG-BH. It has been found advantageous to reclone the clones derived from p52EG into a vector pUC9 that is especially suitable for expression of DNA into protein in bacteria. A smaller plasmid was constructed from p52EG-BH by a complete BamHI and HindIII digest, followed by a partial digestion with XhoI (there are XhoI sites at 0.354 and 0.372). The appropriate gell-eluted fragment (BamHI-XhoI-XhoI or BXX) was subsequently cloned into the BamHI and SalI sites of a second pUC9 vector creating a SalI-XhoI hybrid site at 0.372.

The coordinates of the insert were shown to be 0.345 to 0.372 by restriction mapping and eventually by DNA sequence analysis in the region of 0.368 to 0.348. About one restriction site of three is common to HSV-2 and HSV-1. These sites were used to normalize the coordinates of HG52 to those of the KOS strain of HSV-1. For example, the SalI site at 0.360 and the BstEII site at 0.348 are identical in the two strains.

The HSV-2 derived plasmid p52BXX which is the HSV-2 analog to the HSV-1 plasmid pKBXX, contains approximately 4000 base pairs with about 450 nucleotides beyond the 5' and the 3' ends of the gB mRNA. It extends from a BamHI site near 0.345 to a XhoI site at 0.372 that is within 10 bp of the one at 0.372 in HSV-1. The site is probably at the identical nucleotide in the two genomes. The BamHI site in HSV-2 is about 50 nucleotides to the right of the one in HSV-1.

The following table shows relative locations of restriction sites:

| REPRESENTATIVE RESTRICTION SITES FOR HSV-1 AND HSV-2 BETWEEN 0.345 and 0.372 MAP UNITS | |
|---|---|
| HSV-1(Kos) | HSV-2(HG-52) |
| BamHI 0.345 | 0.3453 |
| BstEII 0.349, 0.355 | 0.349 |
| XmaI 0.347, 0.354, 0.357, 0.3597 | 0.350, 0.3597, 0.371 |
| NruI 0.369 | 0.369 |
| PstI 0.350, 0.3563, 0.368 | 0.356, 0.3563, 0.367, 0.368 |
| XhoI 0.3682, 0.3716 | 0.354, 0.3716 |
| SalI 0.360 | 0.358, 0.360 |
| BalI 0.3575, 0.3675 | 0.3575, 0.3675 |

Table 2 also shows the DNA base and amino acid sequence comparison for HSV-2 and HSV-1 in gB. The HSV-1 nucleotide and amino acid sequences are given and any changes in the HSV-2 sequence (relative to HSV-1) are indicated. HSV-1 gB contains 9 N-linked saccharide addition sites

Of these, 8 are conserved in HSV-2 gB. The asn-pro-thr- in the remaining site at residues 76–78 in HSV-1 is changed to gly-pro-arg in HSV-2. Finally it was observed that there are 5 codons present in HSV-2 that are absent from HSV-1. This is indicated by a space in the sequence for HSV-1 and the inserted sequence for HSV-2 is written above the open space. The HSV-2 gB gene is very homologous to the one in HSV-1.

EXPRESSION OF gB FRAGMENTS

A. EXPRESSION FROM pKBXX

In order to express gB from pKBXX the plasmid can be cleaved, for example, at the unique NruI site at nucleotide 482, and treated with Bal31 (an enzyme preparation that contains both 5' to 3' and 3' to 5' exonuclease activities) to remove most of the 5' non-coding and hydrophobic signal-specifying nucleotides, or about nucleotides 1 to 911. Following religation and transformation of *E. coli*, clones of bacteria can be examined for their ability to produce gB using antibodies that precipitate gB. Note that in pKBXX, HSV-1 sequences have been inserted at a position in the multiple cloning site that corresponds to amino acids 6 to 8 of β-galactosidase (see Table 3). Therefore the gB gene is fused to the β-galactosidase gene at this point. However, gB is not fused to β-galactosidase at its carboxyl-terminal end because of the presence of the chain-termination codon of gB at nucleotide 3498 (Table 2).

Although pKBXX can be used to express essentially all of the mature gB peptide there are a number of reasons why expression of only a portion of antigenically active gB is advisable. First, large membrane proteins containing hydrophobic sequences are often unstable when expressed in bacteria. Second, only about 750 N-terminal amino acids of the total peptide are antigenically active because the remaining residues are inside the membrane and therefore inaccessible to antibodies. Third, the relationship of three-dimensional structure to antigenic acitivty is not known for any protein, so that one cannot predict a single set of sequences that are most likely to have the highest antigenic activity. Therefore, a nested set of DNA plasmids was chosen, each containing a portion of the N-terminal part of gB (beginning beyond the signal region) for the production of antigenically active gB in bacteria.

One set of plasmids involves the use of a 1477-bp BalI restriction fragment extending from nucleotide 637 to 2114 in both the pKBXX and p52BXX. Purified fragment is incubated Bal31 for different lengths of time to remove 0 to about 300 bp from each end of the fragment. Removal of 275 nucleotides from the 5' and gives a new 5' terminus at nucleotides 911 or just at the end of the hydrophobic signal sequence. After Bal31 digestion, nucleotide lengths of about 800 to 1477 bp obtain corresponding to 267 to 492 of the "N-terminal" amino acid of gB. The nested set of fragments is pooled and blunt-end ligated to HindII-digested (blunt-ended) pUC9. Following transformation of bacteria, the progeny of individual bacteria are examined for the production of antigenicaly active gB using a radioimmune assay (see example 7). A plasmid that leads to the production of large amounts of antigenically active gB is identified and its sequence determined to establish the nucleotide coordinates at the ends of the plasmid.

Such fragments and those from an extends portion of the gB gene are used for the vaccine. Antibodies against the gB peptide can be used to quantify virus neutralization. in the event that the gB vaccine is not sufficiently antigenically active, expression will then employ a eukaryotic vector.

One can employ a so-called shuttle vector that replicates its DNA either in bacteria or in eukaryotic cells. The endogenous promoter sequences for gB transcription are eukaryotic in origin. However, it may require the presene of additional viral factors for efficient expression. Therefore, the use of a different promoter is advisable. The HSV-1 sequences of pKBXX can readily be re-cloned onto the eukaryotic expression vector by making use of restriction sites on either site of the HSV-1 insert, for example HindIII and EcoRI.

B. EXPRESSION FROM p52BXX

In order to express gB from p52BXX the plasmid is cleaved, for example, at the unique NruI site at nucleotide 482 and treated with Bal31 (an enzyme preparation that contains both 5' to 3' and 3' to 5' exonuclease activities) to remove 5' non-coding and hydrophobic signal-specifying nucleotides (nucleotides up to or beyond 911). To remove the membrane-spanning hydrophobic sequences (beginning at approximately 3040) the DNA is cleaved with XhoI (a unique site exists at 2672; the XhoI at 1 was converted to a SalI-XhoI hybrid in the construction of p52BXX). The Bal31 (blunt-ended) XhoI fragments were identified by agarose electrophoresis, gel-eluted, and ligated to SmaI, SalI cleaved pUC8 DNA.

The multiple cloning sites in pUC8, namely EcoRI-SmaI-BamHI-SalI-PstI-HindIII are in the opposite orientation as in pUC9, (Table 3); otherwise the vectors are identical. The direction of β-galactosidase RNA and protein syntheses is from left to right. The insertion of the HSV-2 sequences is from Bal31 to XhoI so that its direction of synthesis is also from left to right. Note that SmaI leaves blunt ends. At the SmaI-Bal31 junction all three reading phases are expected since the Bal31 exonuclease cleavage is not synchronous. Since both SalI (GTCGAC) in the multicloning site of pUC8, and XhoI of HSV-2 (CTCGAG), cleave after the first nucleotide of a codon, the correct reading phase is maintained at the 3' junction. Those codons that preserve the β-galactosidase reading phase at the 5' β-galactosidase/HSV-2 junction (about one-third of the total) will express an authentic gB peptide fused to the first six β-galactosidase amino acids. At the 3' HSV-2/β-galactosidase boundary the reading phase is maintained so that the gB sequences are fused, this time at amino acid residue 10. In essence, four amino acid residues of β-galactosidase are replaced with about 500 of gB. The fusion protein uses the endogenous β-galactosidase terminator present in the vector which adds approximately 100 amino acid residues to the C-terminal side of gB residues.

The ligated DNA is used to transform *E. coli*, strain RDP211, and ampicillin-resistant colonies are obtained. The size and orientation of th HSV-2 inserts in these clones are determined by restriction mapping. The average insert size was found to be about 1.5 kb and all inserts were in the correct orientation.

β-galactosidase cleaves lactose, a disaccharide, to glucose and galactose which are used as energy sources for cellular growth. Its synthesis is regulated at the level of RNA synthesis by the presence or absence of lactose (or chemically similar gratuitous inducers that are not metabolized, such as isopropyl-β-D-thio galactoside, IPTG). Regulatory nucleotide sequences are present upstream (5') from the lac promoter (page 7). In order to identify clones with an in-phase gB/β-galactosidase fusion product, cultures were grown in the presence of IPTG and examined using phase microscopy (400 power total magnification) for the presence of inclusion bodies. Some foreign proteins, especially hydrophobic proteins, produced in large quantities in *E. coli*, will aggregate into inclusion bodies that are readily detectable as vacuolar regions within the bacteria. Approximately one-third of the cultures examined (that contained gB inserts) contained inclusion bodies. In these clones, cell division was also inhibited and the cylindrically shaped cells become filamentous with inclusion bodies present at more or less regularly spaced intervals along the filaments. Cultures appeared normal when grown in the absence of inducer.

Samples from cultures grown in the presence and absence of IPTG are prepared for protein analysis using sodium dodecyl sulphate (SDS)-polyacrylamide gel electrophoresis. Cells are pelleted by centrifugation and lysed. The lysis mixture was sedimented to leave the cytoplasmic (soluble) proteins in the supernatant and the membrane (insoluble) proteins in the pellet. The supernatant proteins are subsequently acid-precipitated and pelleted. Pellets from the cytoplasm and membrane fractions are resuspended in similar volumes of electrophoresis sample solution, and aliquots subjected to SDS-electrophoresis. A major band is observed at a mobility corresponding to 65 kd in the membrane fraction of induced cultures. This is the expected size of gB/β-galactosidase fusion product. The band is not detected in the cytoplasmic fractions obtained from induced cultures or from either the membrane or cytoplasmic fractions of uninduced cultures. Membrane fractions from 17 independent clones that contained inclusion bodies when grown in the presence of IPTG gave a major band at a mobility of about 65 kd. By the use of standard marker proteins it is estimated that 15-50 ug of the fusion product protein are obtained from each ml of culture (containing approximately $5 \times 10^8$ cell equivalents).

The immunological reactivity of the 65-kd fusion protein is examined by transferring the electrophoretically separated proteins onto sheets of nitrocellulose, again using electrophoresis as the driving force. Electroblotting is done as prescribed by the manufacturer of the blotting equipment. Nitrocellulose sheets containing the proteins are soaked in preparations of commercially available antibodies to HSV-2 or to HSV-1. These antibody preparations include the IgG fraction of serum and were obtained from rabbits. Antibody is expected to bind preferentially to the 65-kd protein and is detected by an enzyme reaction. A secondary antibody, goat-antirabbit IgG, with horseradish peroxidase covalently linked to the IgG, is added which will bind to the previously bound rabbit IgG. Finally a substrate for the enzyme is added which causes a colored (blue) precipitate to form at the site of the enzyme reaction. A blue band of precipitate is observed at mobility corresponding to 65 kd on the nitrocellulose blots. Its presence is only detected in the membrane fraction of cells grown in the presence of IPTG. The 65-kd protein crossreacts with HSV-1 antibodies although the reaction is not as strong as with the HSV-2 antibodies.

One of the clones containing a plasmid designated p52ΔNX-60 is chosen for further studies. The 5' and 3' ends of the HSV-2 insert are recloned into M13 cloning and sequencing vectors, the DNA sequence was determined at the 5' and 3' junctions in p52ΔNX-60. The HSV-2 insert contains sequences from amino acid residues corresponding to 135 to 629 inclusive of HSV-1 gB (Table 2). This is consistent with the insert size determined from restriction endonuclease analysis (1.5 kg) and with the size of the fusion peptide (65 kd). This insert is shown to be in phase with β-galactosidase-specified codons at the 5' and 3' functions.

For animal tests of the 65-kd peptide product from p52ΔNX-60, larger quantities of protein are required. The isolation procedure for the membrane fraction is scaled up and mg quantities of the 65-kd peptide are loaded onto a preparative electrophoresis apparatus. The apparatus has the capacity to elute proteins from the bottom of the gel and collect fractions in electrode buffer. Fractions are analyzed by analytical SDS-electrophoresis, peak fractions containing the fusion protein are pooled, and the pooled material is dialyzed against a phosphate-buffered saline. Without further concentration the purified 65-kd protein concentration is 100 to 200 ug/ml. This concentration is suitable for introduction into animals following a 1:1 dilution with Freund's adjuvant.

The 65-kd protein extends in the 5' direction to nucleotide 1192 (Table 2). It may also be desirable to isolate additional DNA clones containing more HSV-2 sequences at this end. Therefore, clones with smaller Bal31-produced deletions are constructed. Expression clones derived from pKBXX of HSV-1 can be constructed using similar procedures. The NruI site at 482 is common to HSV-1 and HSV-2.

EXAMPLE 1

Cloning BamHI fragments of HSV-1 (strain KOS) into pBR322 to form BamHI-G

A. Restriction endonuclease treatment

In a plastic, snap cap, Eppendorf vial 1 ul (about 0.5 ug) of pBR322 (Bethesda Research Laboratories), 36 ul (about 5 ug) KOS and 5 ul (8 units/ul) BamHI are digested in 110 ul of restriction buffer 1. Restriction buffer 1 contains 10 mM Tris buffer, pH 7.4, 50 mM sodium chloride, 10 mM magnesium chloride, 10 uM mercaptoethanol and 100 ug/ml nuclease-free bovine serum albumin. Digestion is carried out for 3 hours at 37° C. (It should be noted that excesses in amounts of enzymes and duration of digestion were used. It should be understood to cut DNA, 1 unit will cut 1 ug of *E. coli* λ phage DNA completely in 1 hour at 37° C.).

After digestion, the reaction mixture is diluted to 400 ul with TE (1 mM EDTA, 10 mM Tris, pH 8.0). The solution is heated to 65° C. for 15 minutes to inactivate the restriction endonuclease and then cooled to room temperature. The solution is then extracted twice with an equal volume of a 24:1 mixture of chloroform and 3-methylbutanol to inactivate and remove any remaining enzyme. (An alternative to inactivation of restriction endonucleases by heat is to add sodium dodecyl sulphate (SDS) to about 1% final concentration. Both the SDS and inactived enzyme are separated from DNA by passage through a miniature sephadex column).

After transfer of 240 ul of the residual solution to another plastic vial 60 ul of 5M sodium chloride and 500 ul (about 2 volumes) of cold ethanol are added. The mixture is kept at −75° C. for 30 minutes, centrifuged, and the supernatant is discarded and the DNA pellet is vacuum dried to remove the ethanol.

B. Ligation

The dried pellet is resuspended in 20 ul of ligase buffer (containing 50 mM Tris buffer, pH 7.8, 10 mM magnesium chloride, 20 mM dithiothreitol and 50 ug/ul nuclease-free bovine serum albumin) with 17 ul of 1 mM adenosine triphosphate and 100 units of T4 DNA ligase (Bethesda Research Laboratories #202). The mixture is incubated for 15 hours and used to transform *E. coli* RR1.

C. Transformation

A 20 ml culture of *E. coli* is grown at 37° C. with aeration in V-medium (tryptone 10 gm; yeast extract, 5 gm; NaCl, 7 gm; KCl, 1.5 gm; MgSo$_4$.H$_2$O, 0.5 gm; water, 1l) to an optical density (620 nm) of 0.3. The culture is chilled on ice for 10 to 30 minutes and the cells pelleted (6000 g×5 minutes at 4° C.). The pellet is gently resuspended in 20 ml of cold (4° C.) ST* (25 mM Tris-HCl, pH 7.5, 10 mM NaCl). Cells are pelleted as above and are resuspended gently in 10 ml CAST (25 mM Tris-HCl, pH 7.0; 10 mM NaCl; 50 mM CaCl$_2$·2H$_2$O) and kept on ice for 20 to 30 minutes. The cells are pelleted again and resuspended very gently in 1.35 ml cold (4° C.) CAST in an Eppendorf vial and kept cold until used for transformation (within 0 to 60 minutes).

To 0.2 ml of a cell suspension in CAST is added 0.1 ml of plasmid (0.01 to 10 ug DNA) in CAST and these suspensions are mixed gently and kept on ice for 60 minutes. The mixture is warmed to 37° C. for 2 minutes and then cooled for the same time interval. The contents of the vial are added to 2.7 ml of V-medium in a culture tube and incubated with aeration for 2 to 3 hours to allow the plasmid DNA time to enter the cell and to be expressed (for the protein synthesis from the ampicillin resistance gene specified by the plasmid). At this time the cells are diluted 5, 50 and 500 X in V-medium and 0.2 ml aliquots are spread on the surface of V-amp petri plates (V-medium hardened with 15 gm/l of agar and containing 25 mg/l of ampicillin). The plates are incubated over night at 37° C. and colonies that grow are used to prepare plasmid DNA.

EXAMPLE 2

Plasmid pKBG-BS3

The BamHI-G clone obtained in the preceding example is subjected to restriction enzyme treatment by the procedure of the preceding example. In the following typical reaction using SalI, the restriction buffer used is RB-S which contains Tris buffer: 6 mM, pH 7.4
Sodium chloride: 150 mM
Magnesium chloride: 10 mM
Nuclease-free bovine serum albumin: 100 ug/ml
β-mercaptoethanol: 10 mM Thus, 10 ug of BamHI G are partially digested with about 1 unit of the enzyme SalI for 15 minutes at room temperature, in 25 ul of RB-S restriction buffer. Workup of Example 2 yields the fragment pKBG-BS3, with coordinates from the 0.345 BamHI site to the SalI site at 0.387.

EXAMPLE 3

Plasmid pKBXX

To obtain pKBXX a mixture of 10 ug of pKBG-BS-3 is digested completely with 8 units of BamHI for 2 hours followed by a "partial digest" using 1 unit of XhoI in RB-1. In both cases restriction buffer 1 is used. In a partial digest as used herein, one unit of enzyme is employed for 10 ug of DNA and the reaction time is reduced to 15 minutes.

On agarose electrophoresis a 4.0 Kb band corresponding to the 0.345 to 0.372 Bam HI- XhoI fragment is obtained. This fragment is electroeluted from the gel, extracted with an equal volume of a 24:1 mixture of chloroform to 3-methylbutanol and ethanol precipitated. This fragment is then ligated to BamHI-SalI cut pUC9. Thus pUC9 is first subjected to the actions of BamHI and SalI by the foregoing procedures and then ligated by the general procedure of Example 1 B with the HSV-1 sequences (BamHI to XhoI 0.345 to 0.372 of the fragment electroeluted above) to the corresponding sites.

EXAMPLE 4

Cloning EcoRI fragments of HSV-2 (strain HG52) into EcoRI site of pBR325

A. Restriction endonuclease treatment

In a plastic, snap cap, Eppendorf vial 2 ul (0.4 ug) of pBR325 (Bethesda Research Laboratories), 36 ul (4 ug)

HG52 and 5 ul (40 units) EcoRI are digested in 110 ul of restriction buffer 2. Restriction buffer 2 contains 100 mM Tris buffer, pH 7.4, 50 mM sodium chloride, 10 mM magnesium chloride, 10 mM mercaptoethanol and 100 ug/ml nuclease-free bovine serum albumin. Digestion is carried out for 3 hours at 37° C.

After digestion, the reaction mixture is diluted to 400 ul with TE (1 mM EDTA, 10 mM Tris, pH 8.0). The solution is heated to 65° C. for 15 minutes to inactivate the restriction endonuclease and then cooled to room temperature. The solution is then extracted twice with an equal volume of a 24:1 mixture of chloroform and 3methylbutanol to inactivate and remove any remaining enzyme.

After transfer of 240 ul of the residual solution to another plastic vial there are added 60 ul of 5M sodium chloride and 500 ul (about 2 volumes) of cold ethanol. The mixture is kept at −75° C. for 30 minutes, after which the supernatant is discarded and the DNA pellet is vacuum dried to remove the ethanol.

B. Ligation to produce clone p52EG

The dried pellets are resuspended in 25 ul of ligase buffer (containing 50 mM Tris buffer, pH 7.8, 10 mM magnesium chloride, 20 mM dithiothreitol and 50 ug/ul nuclease-free bovine serium albumin). 20 ul of HSV-2 sample is mixed with 2 ul of pBR325 DNA, 1.5 ul of 10 mM adenosine triphosphate and 50 units of T4 DNA ligase (Bethesda Research Laboratories #202). The mixture is incubated for 16 hours and used to transform $E.\ coli$ RDP145.

EXAMPLE 5

Cloning BamHI-HindIII fragments from p52EG into pUC9 to form p52EG-BH

In a first vial, 20 ul (about 5 ug) of p52EG are digested with 1 ul of BamHI, HindIII and EcoRI in 22 ul of 2X-restriction buffer 1 for 90 minutes at 37° C. Then, 1/9 volume of 1M Tris is added and incubation is continued for 90 more minutes.

In a second vial, 10 ul of pUC9 are incubated for 3 hours at 37° C. with 1 ul of BamHI and HindIII with 45 ul of restriction buffer 1. Restriction buffer 1 contains 10 mM Tris, pH 7.4 and the buffer is otherwise the same as restriction buffer 2. Following digestion, the cut DNAs are separated by electrophoresis on 0.75% agarose gels, the desired bands electroeluted from the agarose and then extracted and ligated as in Example 4 and used to transform $E.\ coli$.

EXAMPLE 6

Isolation of p52BXX from p52EG-BH

In a first vial, 10 ul (about 5 ug) of p52EG-BH are added with 1 ul of BamHI and HindIII in 40 ul of restriction buffer 1 and incubated for 2½ hours at 37° C. Then, 1 unit of XhoI are added and incubation is continued for 15 minutes to cut only one of the two XhoI sites in many of the molecules of p52EG-BH.

In a second vial, 10 ul of pUC9 are digested with 1 ul of BamHI and 2 ul of SalI for 2½ hours at 37° C. in 40 ul of restriction buffer RB-S.

The restriction buffer used is RB-S which contains
Tris buffer: 6 mM, pH 7.4
Sodium chloride: 150 mM
Magnesium chloride: 10 mM
Nuclease-free bovine serum albumin: 100 ug/ml
β-mercaptoethanol: 10 mM The DNAs are separated by agarose electrophoresis, electroeluted, extracted, ligated and used to transform $E.\ coli$ RDP145 as in the preceding Examples. The fragment of p52EG-BH electroeluted contains a 4.0 b fragment that extends from the BamHI site at 0.345 through the XhoI site at 0.353 to the XhoI site at 0.372. It should also be noted that a XhoI site has the same cohesive ends at SalI so that the HSV-2 XhoI site at 0.372 is cloned into the SalI site in pUC9.

EXAMPLE 7

Expression of a gB fragment from pKBXX in bacteria

A. Production of a gB fragment 10 ul of pKBXX DNA (about 10 ug) and 10 ul of BalI restriction endonuclease are added to an equal volume of 2X BalI buffer (restriction buffer RB1 without NaCl) and the DNA is digested for 16 hours at 37° C. in an Eppendorf snap-cap vial. Following the separation of the two DNA fragments (1.48 kb and 5.20 kb) by electrophoresis through a 0.7% agarose gel, the desired 1.48 kb is electroeluted from the gel. The DNA is extracted twice with an equal volume of a 24:24:1 mixture of phenol, chloroform and 3-methylbutanol, respectively, to inactivate and remove remaining BalI enzyme. The aqueous (DNA-containing) phase is brought to 0.15 M sodium acetate (3 M stock solution) and precipitated by the addition of two volumes of cold ethanol and a 30 minute storage period at −75° C.

Ethanol is decanted and the DNA vacuum dried and resuspended in 25 ul of bovine serum albumin at 500 ug/ul, to which is added an equal volume of 2X Bal31 buffer (40 mM Tris, pH 8.0; 24 mM $CaCl_2$, 24 mM $MgCl_2$, 400 mM NaCl, 2 mM EDTA) and 2 ul of Bal31 (2.5 units). These concentrations of enzyme and DNA cause the hydrolysis of about 100 nucleotides/min from each end of the DNA. Bal31 preparations contain both 5' to 3' and 3' to 5' exonucleolytic activity, so that both strands of DNA are hydrolyzed. 5-ul samples are removed at 20 second intervals from 0 to 3 minutes and added to a single Eppendorf snap-cap vial containing 50 ul of phenol-chloroform-3-methylbutanol (see preceding paragraph).

The pooled DNA fragments are extracted and precipitated as before, resuspended in 50 ul of TE, and passed through a Sephadex minicolumn by spin-dialysis to remove remaining mononucleotides with little change in sample volume. To this is added 1 ul of pUC9 vector DNA (about 0.1 ug) that has been blunt-end cleaved by incubation with HincII. Usually 5 ul of 10X ligase buffer with 10 uM ATP (see section 4 for 1X ligase buffer) is added and 3 ul of T4 DNA ligase ($4 \times 10^5$ units/ml). The resulting solution is incubated at room temperature for 16 hrs and used directly to transform $E.\ coli$ as in Example 1C.

B. Antigenically active gB fragment

Bacteria from individual colonies, resulting from the above transformation experiment, are used to inoculate 10 ml cultures and are grown to an optical density (OD) of 0.5. Bacteria from each culture are pelleted and resuspended in 10% trichloroacetic acid (TCA) and the precipitate is washed with the same volume of 10% TCA in Eppendorf snap-cap vials. The final pellet is washed in 100 ul of TE and neutralized by the addition of 2 ul of 2M Tris-base, pH 8.0. 10 ul samples are added to nitrocellulose filters and air-dried for 30 minutes at 37° C. The bacteria, proteins and DNA will remain bound to the filter.

The nitrocellulose strip (145×190 mm) is soaked in 5 ml of buffer A (10 mM Tris, pH 7.5; 170 mM NaCl, 0.1 mM phenylmethylsulfonyl fluoride) and also contains 0.01% SDS, and 10 mM magnesium chloride. DNA is digested for 10 minutes by the addition of 10 ul of a solution of DNaseI at 2 mg/ml. All treatments of the nitrocellulose strip are in an 18×150 mm screw-cap test tube, the nitrocellulose being rolled up inside the tube. The strip is kept bathed in all successive incubations by rotating the test tube on a drum that revolves at about 10 rpm.

DNaseI and nucleotides are removed by 2×5 ml washes for 5 minutes each in buffer A containing 0.01% SDS. Non-specific binding of HSV-1 antibodies is blocked by treatment of the nitrocellulose with 3 ml of buffer A containing 0.01% SDS and 10% horse serum. Treatment is for 3 hours. The strip is washed with 2×5 ml for 10 minutes each in 5 ml buffer A containing 0.01% SDS.

HSV-1 antiserum (typically obtained from Accurate Scientific) is added to allow binding of gB antibodies in the sera to any antigenically active gB fragments present in the bacterial lysates. 10 ul of antiserum is added to 500 ul of solution B (buffer A containing 1 mM EDTA, 0.1% SDS, 0.1% Triton X-100 and 4% horse serum) and allowed to bind for 16 hours at room temperature. After 2×3 ml washes in solution B for 10 minutes, 500 ul of solution B containing 2 uCi of $^{125}$I protein A (New England Nuclear) is added. Protein A is from *Staphylococcus aureus* and binds to the constant region of IgG antibodies. Protein A is allowed to bind to these sites for 3 hours at room temperature. Finally, the filter is washed by 5×5 ml washes for 15 minutes each with solution B without horse serum, dried and exposed to X-Omat X-ray film for 24 to 72 hours.

C. gB fragment for use as an antigen in rabbits

In order to examine the gB product synthesized in bacteria, the gB peptides synthesized from the Bal31-digested DNA (Example 7) and after preparation of the final clones (see Example 8) can be examined by a radioimmune reaction of SDS-electrophoretically separated peptides. Since the gB product is under the control of the lac promoter, its production should be induced by chemicals that induce the synthesis of lac proteins (such as IPTG).

Ten-ml cultures of bacteria are grown in the presence and absence of IPTG to an OD of 0.5, the cells pelleted and resuspended in 1 ml of 10% cold TCA and kept cold for 30 minutes. After a second centrifugation the cells are washed with 10% TCA and the final pellet is neutralized with 2 ul of 2M Tris-base, pH 8.0, and resuspended in 100 ul of electrophoresis sample solution (50 mM Tris, pH 7.0, 2% SDS, 5% β-mercaptoethanol, 0.005% bromphenol blue) 10 ul samples are applied to a 9.5% gel and peptides separated for 6 hours at 100 volts.

The peptides are electroblotted onto a nitrocellulose sheet and the sheet is air-dried. The gB peptide is visualized by treating the nitrocellulose sheet as in Example 7 to assay for the presence of gB by the radioimmune assay. A peptide of the expected size should be visualized.

In order to prepare gB fragment for use as an antigen to be injected into rabbits, induced bacterial cultures can be treated with TCA and resuspended in electrophoresis sample solution, as indicated in the first paragraph, except that all of the volumes are increased tenfold to obtain about 100 ug of gB peptide. gB from the appropriate region of the gel are mashed in Freund's adjuvant and injected into a rabbit for antibody production. 25 ug of peptide can be used in the initial and succeeding booster injections. Subsequently antisera from rabbits are tested for potency to precipitate gB and to neutralize virus and thereby preferred fractions are identified.

EXAMPLE 8

Expression of a gB fragment from p52BXX in bacteria

A. Production of a gB Fraction p52BXX DNA (25 ugm) in an Eppendorf snap cap vial is ethanol precipitated, the pellet washed with 70% ethanol, vacuum dried and resuspended in 45 ul of RB6 (100 mM NaCl, 6mM Tris HCl at a pH of 7.4, 6 mM MgCl$_2$, 5 mM 2-mercaptoethanol, 100 ug/ml BSA). Restriction endonuclease NruI (4 ul at 4 units/ul) is added and the mixture is incubated in bovine serum albumin overnight at 37° C. Stop solution (5 ul) is added and the reaction mixture is subjected to two cycles of spin dialysis using BioGel P-100 in TE buffer to remove inactivated enzyme, and the detergent and dye present in the stop solution. The DNA is ethanol precipitated, washed and dried. DNA is resuspended in 25 ul BSA (500 ug/ml), to which is added an equal volume of 2X Bal31 buffer (40 mM Tris, pH 8.0, 24 mM CaCl$_2$, 24 mM MgCl$_2$, 400 mM NaCl, 2 mM EDTA) and 3 ul of Bal31 (3.5 units). These concentrations of enzyme and DNA cause the hydrolysis of about 150 nucleotides/min from each end of the DNA. Bal31 preparations contain both 5' to 3' and 3' to 5' exonucleolytic activity, so that both strands of DNA are hydrolyzed. 7-ul samples are removed at 30 second intervals from 1½ to 4½ minutes and added to vials containing 43 ul of TE and 5 ul of stop solution. The extent of Bal31 cutting is determined by running 10 ul samples on agarose gels (0.75% gel).

Samples of DNA that appear to be shortened by about 1 kb (500 bp/end) by digestion with Bal31 are subjected to two cycles of spin dialysis. One-tenth of the final volume of 10X RB1 and 1 ul of Xho I (15 units/ul) are added and the mixture is incubated for 8 hrs at 37° C. Xho I cuts the DNA at nucleotide 2672 giving rise to two fragments. 5 ul of stop solution is added and one-half of the DNA from each time point is added to each of two adjacent wells on a 0.75% agarose gel. Electrophoresis is conducted overnight at 54 volts. DNA is visualized by edthidium bromide staining and the 1.7 kb band is cut from the gel and electroeluted (3 hours at 108 volts in 0.1 X electrode buffer). Ethidium bromide is removed by 3 extractions with equal volumes (about 3 ml) of n-butanol saturated with TE. Two extractions with equal volumes of chloroform: 3-methyl-butanol (24:1) are done and the DNA is ethanol precipitated, washed with ethanol and dried.

DNA is resuspended in 50 ul of TE and subjected to two cycles of spin dialysis as is 4 ug of pUC8 vector DNA (previously exposed to successive digestions with SmaI and SalI). Vector DNA is ethanol precipitated, washed and vacuum dried prior to resuspension in 48 ul of SmaI buffer (Tris.HCl (pH b 8.0), 6 mM; KCl, 20 mM; MgCl$_2$, 2-mercaptoethanol, 6 mM; BSA, 100 ug/ml). 2 ul of SmaI (10 units/ul) is added and after digestion the DNA is subjected to two cycles of spin dialysis (on some occasions the SmaI is inactivated and removed by chloroform-3-methylbutanol (24-1) extractions followed by ethanol precipitation and drying the DNA). In either case the DNA is brought to 46 ul in RBS, 4 ul of SalI (10 units/ul) is added and incubation is for 2 hours at 37° C.

The HSV-2 DNA fragment from each time point (about 2 ug) is mixed with 0.2 ug of pUC8 DNA. One-tenth volume of 10X ligase buffer, 1 ul ATP (11 mg/ml and 3 ul of T4 DNA ligase ($4 \times 10^5$ units/ml are added such that the total reaction volume is 50 ul. Ligation is over night at room temperature. The reaction mixture is used directly to transform *E. coli* RDP211 by the technique of Example 1C.

B. Antigenically active gB fragment

Identification and immunological activity of the gB-β-glactosidase fusion protein Individual bacterial colonies are obtained containing plasmids (of the class designated p52ΔNX), with appropriate HSV-2 inserts, and inclusion bodies when grown in the presence of IPTG (isopropyl-β-D-thiogalactoside). Cultures (10 ml) from these colonies are grown in V-medium in the induced stat (4 ul of IPTG at 56 mg/ml in 50% ethanol) or uninduced state (150 ul of 20% (V/V) glucose solution) to an OD of about 1. Cells are pelleted (6000 g×5 min) and resuspended in 100 ul of a lysis buffer (glucose, 50 mM; EDTA, 10 mM; Tris-HCl (pH 8.0), 25 mM) containing 10 mg/ml lysozyme and 4 ug/ml pancreatic DNase I. After 30 minutes incubation on ice the reaction mixture is vortexed, freeze thawed twice and 5 ml TE added and the mixture vortexed. The sample is sedimented (6000 g×10 min) to pellet the membrane or insoluble proteins leaving the cytoplasmic or soluble proteins (including ribosomes) in solution. An equal volume of cold trichloroacetic and (10%, W/V) is added to the supernatant for 30 minutes on ice to precipitate the cytoplasmic proteins. These proteins are sedimented (6000 g×10 min) and resuspended in 100 ul of electrophoresis sample solution (0.05M tris-HCl (pH 7.0), 2% SDS, 5% β-mercaptoethanol, 0.005% bromophenol blue, 5M urea). 5 to 10 ul of 2M tris-base is added to neutralize remaining trichlorocetic acid in the pellet. The membrane proteins present in the first pellet are also solubilized in 100 ul of electrophoresis sample solution.

12% acrylamide gels (analytical gels) are made by dissolving acrylamide (12 gm) and N,N'-diallyltartardiamide (0.56 gm) in 100 ml of gel buffer (0.375M tris.HCl, pH 8.8; SDS, 0.1%). 0.6 ml of an ammonium persulfate solution (1 gm to 9 ml of water) and 30 ul N,N,N',N'-tetramethylethylenediamine are added to 90 ml to catalyze the polymerization process. The solution is degassed under vacuum and 45 ml is used to form each separating gel. The solution is poured between two glass plates (15.9×19 cm) separated by 1.2 mm spacers on each side and a third spacer at the bottom of the plates. The entire assembly is held together and to a plastic gel stand by clamps and the edges are sealed with agarose (1.6 gm/100 ml water). A plastic blank (18 cm wide×2.5 cm long×1.2 mm thick) is inserted to form an even surface at the top of the gel. After the gel is polymerized (1 hour) the blank is removed and 15 ml of a stacking gel (made in the same way but containing only 5% acrylamide and in 0.12M tris.HCl, pH 7.0; 0.1% SDS) is poured on top of the separation gel. A comb with 10 teeth (each 8.5 mm wide×15.2 mm long) is added to the stacking gels. Following polymerization of the stacking gel (1 hour) protein samples (5 to 10 ul) in electrophoresis sample solution are added to each well formed by the teeth of the comb. Gels are electrophoresed at 108 volts for 4.5 hours in tris-glycine electrode buffer (Tris, 0.025M; glycine, 0.192M; SDS, 0.1%; pH 8.5). Following electrophoresis the gel plates are separated and the proteins in the gel are either stained or blotted.

To visualize proteins Coomaisse Brilliant Blue stain (0.25% stain, 9.2% glacial acetic acid, 45.4 % methanol) is added to the gel for ½ hour and then destained in methanol-acetic acid-water (5-7.5-87.5) over night.

Proteins to be used for antibody reactions are not stained but are blotted onto nitrocellulose paper following separation using electrophoresis on 12% polyacrylamide-SDS gels. An electroblotter is used and blotting is done according to instructions supplied by the manufacturer. Blotting is conducted for 1½ hours at 60 volts in an electrode buffer (192 mM glycine, 25 mM tris-HCl, 1% SDS adjusted to a pH of 8.3) containing methanol to 20% (V/V).

After the proteins are transferred to the nitrocellulose it is cut into strips that fit into 100 mm diameter plastic Petri dishes for the antibody binding assay. The strips are rinsed twice with 5 ml phosphate buffered saline (PBS) ($CaCl_2.2H_2O$, 1.14 mg; KCl, 0.2 gm; $NaHPO_4$, 1.02 gm; $KH_2PO_4$, 1.02 gm; $KH_2PO_4$, 0.2 gm; $MgCl_2.6H_2O$, 0.1 gm; NaCl, 8 gm; adjust pH to 7.4) for 5 minutes for each wash. Non-specific binding is minimized by treating the filter strips for 1½ hours with 5 ml PBS containing 500 ul of horse serum. After two washes in 5 ml PBS the strips are exposed over night to commercial anti-HSV-2 (20 ul) or anti-HSV-1 (50 ul) rabbit serum in 5 ml PBS containing 100 ul horse serum. Antiserum is removed by three washes in 5 ml PBS and a second antibody is added in 5 ml PBS and 100 ul horse serum. The second antibody is goat-anti-rabbit IgG which contains covalently conjugated horse radish peroxidase. The second antibody will bind to IgG present in the first antibody (at the site of HSV-2 proteins). The nitrocellulose strips are exposed to the second antibody for 3 hours. After 5 washes in PBS 5 ml of substrate solution (4-chloro-1-naphthol, 10 mg; ethanol, 1 ml; 30% $H_2O_2$, 10 ul; water 100 ml) is added until blue color develops at the site of the indicator enzyme (horse radish peroxidase). All incubations are carried out on a rotary shaker at 75 RPM.

C. gB FRAGMENT

To obtain larger quantities of the 65 kd gB-β-galactosidase fusion protein for animal tests the membrane fraction described above is prepared from liter quantities of induced cultures. A clone containing a plasmid designated p52ΔNX-60 is used. Up to 10 ml of the membrane fraction containing the 65 kd fusion protein (from the equivalent of a 1 l culture) is pipetted onto a 10% polyacrylamide-SDS preparative gel and electrophoresed (150 volts). Proteins are run off the gel and fractions (2 ml) collected over a 6-8 hour time period. Fractions containing the fusion protein are identified by polyacrylamide-SDS gel electrophoresis of the fractions from the preparative gel. 50 ul samples are run on analytical gels and the mobilities compared with those of the unfractionated samples. Proteins are visualized by staining and destaining as indicated above. Relatively pure 65 kd fusion protein is obtained. The protein is dialyzed against PBS and diluted 1 to 1 with Freund's adjuvant. The 65 kd protein is then at a concentration of approximately 100 ug/ml. One ml aliquots are used for injections at multiple sites on the haunches and back of goats and rabbits for antibody production. The regimen employed uses 5 injections at one week intervals with serum collection beginning after 7 weeks.

To demonstrate protection in mice, 10 ul to 100 ul are injected into similar regions of mice. After different time intervals lethal doses of HSV-2 ($5 \times 10^5$ plaque forming units) are injected into related regions of the mice. The protected mice show a significant enhancement in survival rate over controls.

TABLE 1

Nucleotide sequence of HSV-1 gB and surrounding regions
The nucleotide sequence of HSV-1 (KOS) and between 0.372 and 0.345 map units is presented. The sequence originates a XhoI site at 0.372, and terminates at a BamHI site at 0.345 map units. The sequence is written five prime to three prime. Putative "CCAAT" (. . . .), and "TATA" (_) signals are underlined. Three possible mRNA start sites are indicated (*). The first possible AUG translation initiation condon is shown with a box and arrow. The end of translation from the AUG condon is designated with the word END. A putative polyadenylation signal AATAAA (black squares) is indicated, and shortly after a putative point of polyA addition is marked ( ).

```
          10        20        30        40        50        60      · 70        80
CTCGABAAGATECTBCBTCSTCABCBTCCABBCGAGSTGTBCCBCGACETTCECCBCBGTCTCBCCAACGGTTTBCGGC
XhoI 90       100       110       120       130       140       150       160
BCBCBCCGGTTCTBCCBCCTGACBGCBBGCGGGGCACGGTACTCAGCAACCGCTCGGCGCCGCGTSTTCGACECGCGCA 170       180       190       200       210       220       230       240
CCGGTTCATECGAGCBTCTTCCTGCGACACACCAGCTGACCEGCCTTGCTCCCAGCATCACCATCGCTTCTTCTTGAGC 250       260       270       280       290       300       310       320
TCGTCAACGGCCCCTCTTTTGATCACTCACCCCACAGCTTCGCCCAGCCCCCCAACACCECGCTGTATTACAGCGTGAG 330       340       350       360       370       380       390       400
AACGTGGGGCTCCTECCETCACCTGAAGACACCAGCTGACCEGCCTGGAGGAGCTCGCCCGGTTCATCATEGGTTGBBC 410       420       430       440       450       460       470       480
CBTCCCAATTTCAGGGGTTTACTGTTTTGACGGCATTTCCCAACTAACGCCCACTCAGCGCGTGGCGACATTATAAGC
   ....                              ....

490       500 **  *  510       520       530       540       550       560
TTCGCGAGCTGTTATCGCCACCACACTCTTTGCCTCGGTCTACCGGTGCGGGGAGCTCGAGTTGCGCCGCCGECACTGC 570       580       590       600       610       620       630       640
ABCCGCCCCGACCTCCEAGTECTTACCGCTTACCGECGCATATACTTCATCGACTCGCATTETCCGTGCTECEGGCGGC 650       660       670       680       690       700       710       720
CATCGTCGAGAECECCCCTTCCTGCGACACACCAGCTGACCEGCCTTGCTCCCAGCATCACCATGTTTCTCBATCCTCT 730       740       750       760       770       780       790       800
ACTCGTCCTTCCABACCTCCCCTGCGACACACCAGCTGACCEGCCTTGCTCCCAGCATCACCATCGCTTCTTCTTGAGC 810       820       830       840       850       860       870       880
CBCCCCTCBTBBBBCCTCTTATBBCGACACACTTGCTGACCEGCTTTGCTCCCAGCABBBTCCTBTBBCBGTCBBGCGG 890       900       910       920       930       940       950       960
CTCCBAGTTCCCCBBCABCTCCTBCGACTCBCBAGCTGACCEGCCTTGCTCCCAGCATCACCATCGCTTCTTCTTGBCC 970       980       990      1000      1010      1020      1030      1040
CTTBGCBCCCCCAACGGGGACCCBAAACCBAAGAABAACAAAAACCCGCTCCCAGCATCACCATCGCTTCTTCTTGCGG 1130      1140      1150      1160      1170      1180      1190      1200
ACTTTTACGBTBCCCACCCCACBGGCACACACCAGCTTTBABCABGTGCTCCCAGCATCCCCATCGCTTCTTCTTGGAE 1210      1220      1230      1240      1250      1260      1270      1280
BBTCABAATTACACBGAGGGCATCBCBTTCTTCAAGGGACCECCCTTTCACCCAGCATCACCATCGCTTCTTCTTACTA 1290      1300      1310      1320      1330      1340      1350      1360
CAAAGACBTCACCBTTCBCAGBTBTBBCTTCBBCCACCCBTACTCCCABTTTABBGGATCTTTBCGCACBCBBCCCCCG 1370      1380      1390      1400      1410      1420      1430      1440
TCCCCTTCBBABGABBTBATCBACAABAAABACTBCTGGGATCCCTTCBBTCCABCATCACCATCGCBCBCAACAACTG 1450      1460      1470      1480      1490      1500      1510      1520
BABACCCACBCBTTTTACTCCBAGGABACCACCAGCTGACCEBCCTAAACCBBAGCATCACCATCGCACCBACCCGCCG 1530      1540      1550      1560      1570      1580      1590      1600
BGGCTBBCACACCACCBACCTCAAGTACAACCCCTCGCGGGTBGAGGCGTTCCACCGGTACGGGACGGGACAAACTGCA 1610      1620      1630      1640      1650      1660      1670      1680
TCGTTACATECGAGCGTCTTCCTGCGACACACCAGCTGACCEGCCTTGCTCCCAGCATCACCATCGCTTCTTCTTGTCC 1690      1700      1710      1720      1730      1740      1750      1760
CCBTTTTACECBAGBBBCTTCGTBACCCGAACCABCTACCACCGCCBAACBTCCBACCBTTCAACASGBCTCBAGGCTT
```

TABLE 1-continued

|  |  |  |  |  |  |  |  |
|---|---|---|---|---|---|---|---|
| 1770 | 1780 | 1790 | 1800 | 1810 | 1820 | 1830 | 1840 |

CTACGCBCBBACCTCACCACCAABBCCCBBBCCACGGCGCCGACCACCCBGAACCCATCACCATCCCCAABTTCAACCG

|  |  |  |  |  |  |  |  |
|---|---|---|---|---|---|---|---|
| 1850 | 1860 | 1870 | 1880 | 1890 | 1900 | 1910 | 1920 |

TBGTTCCTTGATBBGTCCAAABCBCCCBTCEBTCBCACACCATBACCAABTGGCGAABTBBACGGAGATBCTCTBCTCC

|  |  |  |  |  |  |  |  |
|---|---|---|---|---|---|---|---|
| 1930 | 1940 | 1950 | 1960 | 1970 | 1980 | 1990 | 2000 |

GASTACBBTCTCCBACTCTTCCTGCGACACACCABCTGACCEGCCTTGCTCCCAGCATCACCATCGCTTCTTCTTCCTC

|  |  |  |  |  |  |  |  |
|---|---|---|---|---|---|---|---|
| 2010 | 2020 | 2030 | 2040 | 2050 | 2060 | 2070 | 2080 |

BCBSCGTATECBAGCGTCTTCCACCGACTCTTCAGCTBACCEGCCTTGCTCCCAGCATCACCATCGCTTCCAAACBCGA

|  |  |  |  |  |  |  |  |
|---|---|---|---|---|---|---|---|
| 2090 | 2100 | 2110 | 2120 | 2130 | 2140 | 2150 | 2160 |

CGCACACATBCGAGCBCCATTTBACGACACACCABCTBACCEGCCTTGCTCCCAGCATCACCATCGCTTCTTCTTGAAC

|  |  |  |  |  |  |  |  |
|---|---|---|---|---|---|---|---|
| 2170 | 2180 | 2190 | 2200 | 2210 | 2220 | 2230 | 2240 |

ACGCTACBTCTCCTAABGCTCCTGCGACCACCAABGCBACCTGCCTAGCCCCCAGAAACCCCACCCCCACCBCCCBCGB

|  |  |  |  |  |  |  |  |
|---|---|---|---|---|---|---|---|
| 2500 | 2260 | 2270 | 2280 | 2290 | 2300 | 2310 | 2320 |

BGCCTACAACCBTCATCAAAAGACCCCAACCTCCTCCTCCCGAGTTTGCTCCCAGCATCACCATCGCTTCTTCACAACC

|  |  |  |  |  |  |  |  |
|---|---|---|---|---|---|---|---|
| 2330 | 2340 | 2350 | 2360 | 2370 | 2380 | 2390 | 2400 |

ACATACAGSCATBTABTATBTTBBBCCBBCBTBBGAGCTACTACABAATCABAGTCATCABCACCGCTTCTTABCCCTB

|  |  |  |  |  |  |  |  |
|---|---|---|---|---|---|---|---|
| 2410 | 2420 | 2430 | 2440 | 2450 | 2460 | 2470 | 2480 |

TGGAACGAGCCCGAABCCCCAABCCATCACACCABCTGACCEGCCTBGCTCCCAGGAGGTBACTCGCTTCTTCBCTCBB

|  |  |  |  |  |  |  |  |
|---|---|---|---|---|---|---|---|
| 2490 | 2500 | 2510 | 2520 | 2530 | 2540 | 2550 | 2560 |

CBACGTGATGGCCBCGTCTBCCBGTCGTGTCCBGTCGCBTATCECTGATTCCCAGCATCAAAACATCBCTATCGCTCBC

|  |  |  |  |  |  |  |  |
|---|---|---|---|---|---|---|---|
| 2570 | 2580 | 2590 | 2600 | 2610 | 2620 | 2630 | 2640 |

GGCCCGGGGCCTBTACABCCCCCTGBTCACACCAGCTGACCEGCCTABCTTCBBTACGAAGACCGAGGBGCABCTGGGG

|  |  |  |  |  |  |  |  |
|---|---|---|---|---|---|---|---|
| 2650 | 2660 | 2670 | 2680 | 2690 | 2700 | 2710 | 2720 |

BAGAACAACGAGTBCBBCTGACBCBATCBCGATCGAGCCGTBCACCBGGGACACCBBGACACBCTACTTCCTTCBGTGG

|  |  |  |  |  |  |  |  |
|---|---|---|---|---|---|---|---|
| 2730 | 2740 | 2750 | 2760 | 2770 | 2780 | 2790 | 2800 |

BBBCTACBTBTACTTCAGGACBCBTACTCCCACCBCTABTGABCCBGCCBACABTCCACCACCBBTCAGACCTTCATCG

|  |  |  |  |  |  |  |  |
|---|---|---|---|---|---|---|---|
| 2810 | 2820 | 2830 | 2840 | 2850 | 2860 | 2870 | 2880 |

ACCTCAACATCACCATBCTGGABGATCACGABTTTBTCCCCTBGABGTBSBTACACATCACCATATCAABBGACAGBBC

|  |  |  |  |  |  |  |  |
|---|---|---|---|---|---|---|---|
| 2890 | 2900 | 2910 | 2920 | 2930 | 2940 | 2950 | 2960 |

CTBCTBGACTACACGBGAGGTCCABCBCCBCAACCABTBCACBACCBCTTCBCACCATCACCATCACGBTCATCCACBC

|  |  |  |  |  |  |  |  |
|---|---|---|---|---|---|---|---|
| 2970 | 2980 | 2990 | 3000 | 3010 | 3020 | 3030 | 3040 |

CGACBCCAACBCCBCCATSTTCBCBBBCBBBCBCBCTTCTTCBABBBGATBBBCGACCTBGGGCGCGCGGTCBBCAAGG

|  |  |  |  |  |  |  |  |
|---|---|---|---|---|---|---|---|
| 3050 | 3060 | 3070 | 3080 | 3090 | 3100 | 3110 | 3120 |

TBBTGATBBCATCBTBBCGGTATCBBACBTCGGBTBTTBTCCTTCTTCATBTCCAACCCCTTTTCTTTTBBBBGCBCTG

|  |  |  |  |  |  |  |  |
|---|---|---|---|---|---|---|---|
| 3130 | 3140 | 3150 | 3160 | 3170 | 3180 | 3190 | 3200 |

BCCBTBBBTCTBTTBBTCCTBBCCGGCCTGGCBBCCTTCTTCBCCTTTCBTTACBTCATBCBBTBBCTBCGAGCAACCC

|  |  |  |  |  |  |  |  |
|---|---|---|---|---|---|---|---|
| 3210 | 3220 | 3230 | 3240 | 3250 | 3260 | 3270 | 3280 |

CATGAAGGCCCTBTACCCTCTAACCACCACACCAGCTGACCEGCCTTGCTCCCAGCATCACCATGGGAGGGCBGAGAGG

|  |  |  |  |  |  |  |  |
|---|---|---|---|---|---|---|---|
| 3290 | 3300 | 3310 | 3320 | 3330 | 3340 | 3350 | 3360 |

BCGGCGAATTTBACCCAABTAGAGABACBACCAATCTBCCGTBACCTGBATCCAGBTCBCCACACGGGCATGGGACCGC

|  |  |  |  |  |  |  |  |
|---|---|---|---|---|---|---|---|
| 3370 | 3380 | 3390 | 3400 | 3410 | 3420 | 3430 | 3440 |

ACBAGGAACAABBAABBAGTCCTGBBACBCACCAACTCACBACAATBACAGCCAGCATCACCATCGCCATGCAACBCCB

|  |  |  |  |  |  |  |  |
|---|---|---|---|---|---|---|---|
| 3450 | 3460 | 3470 | 3480 | 3490 | 3500 | 3510 | 3520 |

CAACACCCAACTACACCCAAGTTCCCAACAAAGACGGTACCEGCCTTGCTCCCAGCATCACCATCGCTTCTTCTT<u>AAAT</u>
<div style="text-align:center">END</div>

|  |  |  |  |  |  |  |  |
|---|---|---|---|---|---|---|---|
| 3530 | 3540 | 3550 | 3560 | 3570 | 3580 | 3590 | 3600 |

<u>AAAA</u>ACCACGGGTATTAAACCGCAAACCACACCAGCTGATTTTTCTTGCTCCCAGCCTTTBCATGTBTBTGGGAAGAAA

|  |  |  |  |  |  |  |  |
|---|---|---|---|---|---|---|---|
| 3610 | 3620 | 3630 | 3640 | 3650 | 3660 | 3670 | 3680 |

BAAAAACATCCCCAAATCTTCCTGCGACCTTTCTTCTAAAAEGCCTTGCTCCCCGCATCACCATCGGGAATTCCCCTTG

|  |  |  |  |  |  |  |  |
|---|---|---|---|---|---|---|---|
| 3690 | 3700 | 3710 | 3720 | 3730 | 3740 | 3750 | 3760 |

BCTASTEATCCGACCCCCCABCCTTCCTACBTAABCTtACCEGCCTTGCTCCCAGCATCACCATAATABCTTACCBACC

|  |  |  |  |  |  |  |  |
|---|---|---|---|---|---|---|---|
| 3770 | 3780 | 3790 | 3800 | 3810 | 3820 | 3830 | 3840 |

CTCCCAAATAAAAACGTCTACAAGCGACACACCAGCTGACCEATTTTGCTCCCAGCATCACCATCAAAACTACTTGAAG

|  |  |  |  |  |  |  |  |
|---|---|---|---|---|---|---|---|
| 3850 | 3860 | 3870 | 3880 | 3890 | 3900 | 3910 | 3920 |

ACTTTACATECGAGCGTCTTCCTGCGACACACCAGCTGACCEGCCTTGCTCCCAGCATCACCATCGCTTCTTCTTGCCB

TABLE 1-continued

```
       3930       3940       3950       3960       3970       3980       3990       4000
TSTCAACBTECGAGCGTCTTCCTGCGACACACCAGCTGACCEGCCTTGCTCCCAGCATCACCATCGCTTCTTCTGATCC
                                                                            BamHI
```

TABLE 2

Comparison of amino acid sequences of HSV-1 and of HSV-2 gB. Listed on the bottom line is the amino acid sequence for HSV-1 gB. The line above that represents the nucleotide sequence for HSV-1 gB. Immediately above that line are shown nucleotides for HSV-2 gB only where they are different from those shown for HSV-1. X indicates those sequences of HSV-2 gB that remain to be determined (corresponding to residues 17–41 of HSV-1 gB). The fourth line from the bottom shows the corresponding amino acid for HSV-2 gB where they are different from those of HSV-1 gB. The numbers at the top are the numbers of the amino acid residues for HSV-1 gB. It will be noted that five extra amino acid residues are present for HSV-2 gB at the gaps shown in the HSV-1 sequence.

```
1                                          10                                         20
    arg gly gly gly leu ile cys ala leu val val gly ala leu val
    G   GG          G   G   TTG ATT     C   C       TG  GTC GT  GGG    CG  CTG GT  XXX XXX XXX XXX
ATG CAC CAG GGC GCC CCC TCG TGG GGG CGC CGG TGG TTC GTC GTA TGG GCG CTC TTG GGG
met his gln gly ala pro ser trp gly arg arg trp phe val val trp ala leu leu gly 30                                         40
XXX XXX XXX XXX XXX XXX XXX XXX XXX XXX XXX XXX XXX XXX XXX XXX XXX XXX XXX XXX XXX
TTG ACG CTG GGG GTC CTG GTG GCG TCG GCG GCT CCG AGT TCC CCC GGC ACG CCT GGG GTC
leu thr leu gly val leu val ala ser ala ala pro ser ser pro gly thr pro gly val 50                                         60
                                ser pro val pro ala           pro arg pro glu pro
XXX                              T   CC  GT  CCG C             C   CGT CC  AG  C
GCG CGC GAC CCA GGC GGC GAA CGG GGG CCC TGC CAC TCC GGC GCC GCC GCC CTT GGC GCC
ala arg asp pro gly gly glu arg gly pro cys his ser gly ala ala ala leu gly ala 70                                         80
arg asp his gln gly     glu ala glu asn gln     arg     ser gly     arg arg
CG  GAC CAC CAA G       G   G   GA  C   A       CGC     A GC GG     G   G   G   C
GCC CCA ACG GGG GAC CCG AAA CCG AAG AAG AAC AAA AAA CCG AAA AAC CCA ACG CCA CCA
ala pro thr gly asp pro lys pro lys lys asn lys lys pro lys asn pro thr pro pro 90                                        100
    asp ala                                                         val     ala
    A   C               C               C                           G       C
CGC CCC GCC GGC GAC AAC GCG ACC GTC GCC GCG GGC CAC GCC ACC CTG CGC GAG CAC CTG
arg pro ala gly asp asn ala thr val ala ala gly his ala thr leu arg glu his leu 110                                       120
    glu     val     ala         gln
    A       TC      G           C C  G                                  G       G
CGG GAC ATC AAG GCG GAG AAC ACC GAT GCA AAC TTT TAC GTG TGC CCA CCC CCC ACG GGC
arg asp ile lys ala glu asn thr asp ala asn phe tyr val cys pro pro pro thr gly 130                                       140
            T                                       G   C   G           G
GCC ACG GTG GTG CAG TTC GAG CAG CCG CGC CGC TGC CCG ACC CGG CCC GAG GGT CAG AAC
ala thr val val gln phe glu gln pro arg arg cys pro thr arg pro glu gly gln asn 150                                       160
                                                                A
TAC ACG GAG GGC ATC GCG GTG GTC TTC AAG GAG AAC ATC GCC CCG TAC AAG TTC AAG GCC
tyr thr glu gly ile ala val val phe lys glu asn ile ala pro tyr lys phe lys ala 170                                       180
                                G   G
ACC ATG TAC TAC AAA GAC GTC ACC GTT TCG CAG GTG TGG TTC GGC CAC CGC TAC TCC CAG
thr met tyr tyr lys asp val thr val ser gln val trp phe gly his arg tyr ser gln 190                                       200
      A   C                           T                                            T
TTT ATG GGG ATC TTT GAG GAC CGC GCC CCC GTC CCC TTC GAG GAG GTG ATC GAC AAG ATC
phe met gly ile phe glu asp arg ala pro val pro phe glu glu val ile asp lys ile 210                                       220
                                                                        met
              C   C                                      G              A
AAC GCC AAG GGG GTC TGT CGG TCC ACG GCC AAG TAC GTG CGC AAC AAC CTG GAG ACC ACC
asn ala lys gly val cys arg ser thr ala lys tyr val arg asn asn leu glu thr thr 220                                       240
                                                                    lys val
                                    C   G                       G   G T     C   G
GCG TTT CAC CGG GAC GAC CAC GAG ACC GAC ATG GAG CTG AAA CCG GCC AAC GCC GCG ACC
ala phe his arg asp asp his glu thr asp met glu leu lys pro ala asn ala ala thr
```

TABLE 2-continued

```
                                       250                                                 260
                  G
CGC ACG AGC CGG GGC TGS CAC ACC ACC GAC CTC AAS TAC AAC CCC TCG CGG GTG GAG GCG
arg thr ser arg gly trp his thr thr asp leu lys tyr asn pro ser arg val glu ala 270                                                 280
    T           C           C                                       G
TTC CAC CGG TAC GGG ACG ACG GTA AAC TGC ATC GTC GAG GAG GTG GAC GCG CGC TCG GTG
phe his arg tyr gly thr thr val asn cys ile val glu glu val asp ala arg ser val 290                                                 300
        T                                   G
TAC CCG TAC GAC GAG TTT GTG CTG GCG ACT GGC GAC TTT GTG TAC ATG TCC CCG TTT TAC
tyr pro tyr asp glu phe val leu ala thr gly asp phe val tyr met ser pro phe tyr 310                                                 320
              G
GGC TAC CGG GAG GGG TCG CAC ACC GAA CAC ACC ACG TAC GCC GCCGAC CGC TTC AAG CAG
gly tyr arg glu gly ser his thr glu his thr thr tyr ala ala ala arg phe lys gln 330                                                 340
                                                                        T       G
GTC GAC GGC TTC TAC GCG CGC GAC CTC ACC ACC AAG GCC CGG GCC ACG GCG CCG ACC ACC
val asp gly phe tyr ala arg asp leu thr thr lys ala arg ala thr ala pro thr thr 350                                                 360
            val
    C       G       G               T                               G       A
CGG AAC CTG CTG ACG ACC CCC AAG TTC ACC GTG GCC TGG GAC TGG GTG CCA AAG CGC CCG
arg asn leu leu thr thr pro lys phe thr val ala trp asp trp val pro lys arg pro 370                                                 380
ala                                                                 ala
G                                           G                   C   G
TCG GTC TGC ACC ATG ACC AAG TGG CAG GAA GTG GAC GAG ATG CTG CGC TCC GAG TAC GGC
ser val cys thr met thr lys trp gln glu val asp glu met leu arg ser glu tyr gly 390                                                 400
        C                               C   G
GGC TCC TTC CGA TTC TCC TCC GAC GCC ATA TCC ACC ACC TTC ACC ACC AAC CTG ACC GAG
GLY ser phe arg phe ser ser asp ala ile ser thr thr phe thr thr asn leu thr glu 410                                                 420
    ser                                         arg         glu         ile
    T           C           C                   CG      T       G           C
TAC CCG CTC TCG CGC GTG GAC CTG GGG GAC TGC ATC GGC AAG GAC GCC CGC GAC GCC ATG
tyr pro leu ser arg val asp leu gly asp cys ile gly lys asp ala arg asp ala met 430                                                 440
    met         lys
    G       G   A               C
GAC CGC ATC TTC GCC CGC AGG TAC AAC GCG ACG CAC ATC AAG GTG GGC CAG CCG CAG TAC
asp arg ile phe ala arg arg tyr asn ala thr his ile lys val gly gln pro gln tyr 450                                                 460
    gln     thr
    A       CG          C   C                   C                                   C
TAC CTG GCC AAT GGG GGC TTT CTG ATC GCG TAC CAG CCC CTT CTC AGC AAC ACG CTC GCG
tyr leu ala asn gly gly phe leu ile ala tyr gln pro leu leu ser asn thr leu ala 470                                                 480
            tyr met                                 gly     ala
            G T A   G                               GG      T G
GAG CTG TAC GTG CGG GAA CAC CTC CGA GAG CAG AGC CGC AAG CCC CCA AAC CCC ACG CCC
glu leu tyr val arg glu his leu arg glu gln ser arg lys pro pro asn pro thr pro 488                                                 498
ala     leu arg glu     pro
GCG     A T GG  A       G CCC
        CCG CCG CCC GGG GCC         AGC GCC AAC GCG TCC GTG GAG CGC ATC AAG ACC ACC TCC
        pro pro pro gly ala         ser ala asn ala ser val glu arg ile lys thr thr ser 508                                                 518
    G                               T                                   C   G           C
TCC ATC GAG TTC GCC CGG CTG CAG TTT ACG TAC AAC CAC ATA CAG CGC CAT GTC AAC GAT
ser ile glu phe ala arg leu gln phe thr tyr asn his ile gln arg his val asn asp
```

TABLE 2-continued

```
                528                                                                538
              ile   val
         C    G   ATC   G                              G      C              T
ATG TTG GGC CGC GTT GCC ATC GCG TGG TGC GAG CTA CAG AAT CAC GAG CTG ACC CTG TGG
met leu gly arg val ala ile ala trp cys glu leu gln asn his glu leu thr leu trp 548                                             558
                                                          ala
                   C                                  C   C          C
AAC GAG GCC CGC AAG CTG AAC CCC AAC GCC ATC GCC TCG GTC ACC GTG GGC CGG CGG GTG
asn glu ala arg lys leu asn pro asn ala ile ala ser val thr val gly arg arg val 568                                             578
                                          ala                               pro
         C        A        C                                 C              C
AGC GCG CGG ATG CTC GGC GAC GTG ATG GCC GTC TCC ACG TGC GTG CCG GTC GCC GCG GAC
ser ala arg met leu gly asp val met ala val ser thr cys val pro val ala ala asp 588                                             598
                                   val                    thr
         G   G                G                    G     ACG
AAC GTG ATC GTC CAA AAC TCG ATG CGC ATC AGC TCG CGG CCC GGG GCC TGC TAC AGC CGC
asn val ile val gln asn ser met arg ile ser ser arg pro gly ala cys tyr ser arg 608                                             618
                                              ile
                                          C   A                                C
CCC CTG GTC AGC TTT CGG TAC GAA GAC CAG GGC CCG TTG GTC GAG GGG CAG CTG GGG GAG
pro leu val ser phe arg tyr glu asp gln gly pro leu val glu gly gln leu gly glu 628                                             638
                                       leu
              C    C    C         C    C                                    C
AAC AAC GAG CTG CGG CTG ACG CGC GAT GCG ATC GAG CCG TGC ACC GTG GGA CAC CGG CGC
asn asn glu leu arg leu thr arg asp ala ile glu pro cys thr val gly his arg arg 648                                             658
         ile
         T         C                                                      T
TAC TTC ACC TTC GGT GGG GGC TAC GTG TAC TTC GAG GAG TAC GCG TAC TCC CAC CAG CTG
tyr phe thr phe gly gly gly tyr val tyr phe glu glu tyr ala tyr ser his gln leu 668                                             678
              val
    T         G                                            G
AGC CGC GCC GAC ATC ACC ACC GTC AGC ACC TTC ATC GAC CTC AAC ATC ACC ATG CTG GAG
ser arg ala asp ile thr thr val ser thr phe ile asp leu asn ile thr met leu glu 688                                             698
    C              G             C        G
GAT CAC GAG TTT GTC CCC CTG GAG GTG TAC ACC CGC CAC GAG ATC AAG GAC AGC GGC CTG
asp his glu phe val pro leu glu val tyr thr arg his glu ile lys asp ser gly leu 708                                             718
                                                                      T
CTG GAC TAC ACG GAG GTC CAG CGC CGC AAC CAG CTG CAC GAC CTG CGC TTC GCC GAC ATC
leu asp tyr thr glu val gln arg arg asn gln leu - his asp leu arg phe ala asp ile 728                                             738
              arg                                                    cys
              G                                                   G  T
GAC ACG GTC ATC CAC GCC GAC GCC AAC GCC GCC ATG TTC GCG GGC CTG GGC GCG TTC TTC
asp thr val ile his ala asp ala asn ala ala met phe ala gly leu gly ala phe phe 748                                             758
                                                                val
         G   T                              A    C         G  A        G
GAG GGG ATG GGC GAC CTG GGG CGC GCG GTC GGC AAG GTG GTG ATG GGC ATC GTG GGC GGC
glu gly met gly asp leu gly arg ala val gly lys val val met gly ile val gly gly 768                                             778
    G         C                      T                        C                 T
GTG GTA TCG GCC GTG TCG GGC GTG TCC TCC TTC ATG TCC AAC CCC TTT GGG GCG CTG GCC
val val ser ala val ser gly val ser ser phe met ser asn pro phe gly ala leu ala 788                                             798
                                   val                                        leu
    G         C                    TC                           C   C          C
GTG GGT CTG TTG GTC CTG GCC GGC CTG GCG GCG GCC TTC TTC GCC TTT CGT TAC GTC ATG
val gly leu leu val leu ala gly leu ala ala ala phe phe ala phe arg tyr val met
```

TABLE 2-continued

```
                                    806                                     818
gln         arg                                                             leu
 AA        A C      T                     T       C               A         CTT
CGG CTG CAG AGC AAC CCC ATG AAG GCC CTG TAC CCT CTA ACC ACC AAG GAG CTC AAG ATG
arg leu gln ser asn pro met lys ala leu tyr pro leu thr thr lys glu leu lys asn 828                                     835
    asp pro gly gly val gly                             ala glu gly gly gly
    GA  CC  GG   G   T  GG          G       A           CG   G GGG GGC GGG
CCC ACC AAC CCG GAC GCG TCC GGG GAG GGC GAG GAG GGC GGC GAC             TTT GAC
pro thr asn pro asp ala ser gly glu gly glu glu gly gly asp             phe asp 845                                     855
             T G             C A  A         C   A   T       TT
GAG GCC AAG CTA GCC GAG GCC AGG GAG ATG ATA CGG TAC ATG GCC CTG GTG TCG GCC ATG
glu ala lys leu ala glu ala arg glu met ile arg tyr met ala leu val ser ala met 865                                     875
                            arg                     ala             ser
                             GA                     GCC             T
GAG CGC ACG GAA CAC AAG GCC AAG AAG AAG GGC ACG AGC CGG CTG CTC AGC GCC AAG GTC
glu arg thr glu his lys ala lys lys lys gly thr ser arg leu leu ser ala lys val 885                                     895
    asn         leu                 asn lys ala arg     ser pro leu his     glu
    A          T C                  AA   AG  GG         T T CGC C A         G G
ACC GAC ATG GTC ATG CGC AAG CGC CGC AAC ACC AAC TAC ACC CAA GTT CCC AAC AAA GAC
thr asp met val met arg lys arg arg asn thr asn tyr thr gln val pro asn lys asp 896                         903
glu ala gly             glu
 AG  C  GA                  G  C  A
GGT GAC GCC GAC GAG GAC GAC CTG TGA
gly asp ala asp glu asp asp leu
```

TABLE 3

The multiple cloning site in pUC9 and pUC8.
A multiple cloning site containing the indicated restriction sites is shown in the figure. The cloning site is near the N-terminal end of the β-galactosidase gene and results in the insertion of 11 amino acids between amino acids 4 and 5 of this protein for pUC9 and between amino acids 6 and 7 for pUC8. The new amino acids are offset from the normal β-galactosidase amino acids. The direction of RNA and protein synthesis is from left to right.

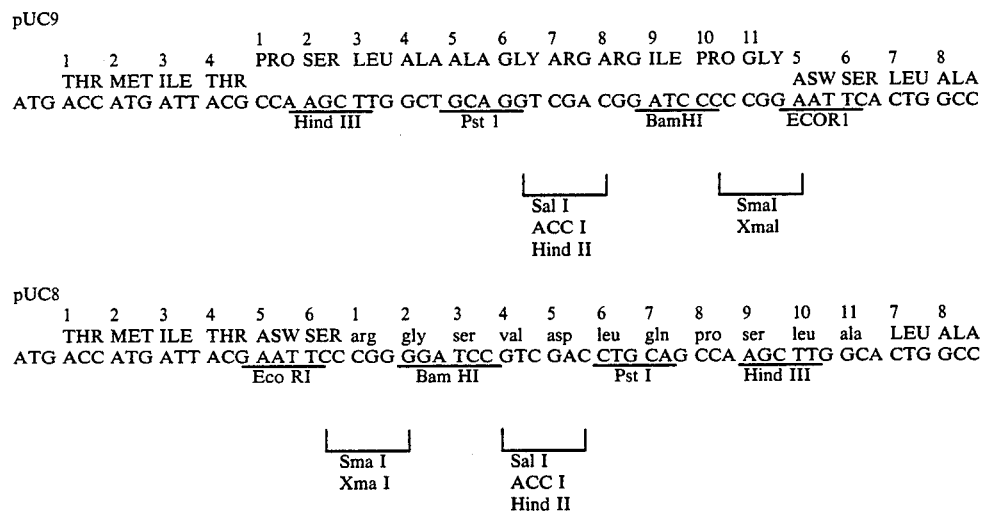

```
pUC9
                     1   2   3   4   5   6   7   8   9   10  11
    1   2   3   4    PRO SER LEU ALA ALA GLY ARG ARG ILE PRO GLY 5   6   7   8
    THR MET ILE THR                                          ASW SER LEU ALA
ATG ACC ATG ATT ACG CCA AGC TTG GCT GCA GGT CGA CGG ATC CCC CGG AAT TCA CTG GCC
                         Hind III    Pst 1           BamHI       ECOR1

|_____|         |_____|
                                        Sal I           SmaI
                                        ACC I           Xmal
                                        Hind II pUC8
    1   2   3   4   5   6   1   2   3   4   5   6   7   8   9   10  11  7   8
    THR MET ILE THR ASW SER arg gly ser val asp leu gln pro ser leu ala LEU ALA
ATG ACC ATG ATT ACG AAT TCC CGG GGA TCC GTC GAC CTG CAG CCA AGC TTG GCA CTG GCC
                     Eco RI     Bam HI           Pst I       Hind III

|_____|         |_____|
                          Sma I           Sal I
                          Xma I           ACC I
                                          Hind II
```

What is claimed is:

1. A substantially pure non-glycosylated amino acid chain comprising a sequence corresponding to that occurring in glycoprotein B of HSV-1 or HSV-2 virus which is antigenic to HSV-1 of HSV-2, which contains no more than 750 amino acid residues, and which includes amino acid residues 135–649 inclusive referened to Table 2.

2. An amino acid chain of claim 1, which has a molecular weight of about 65,000 daltons.

* * * * *